United States Patent
Ranjan et al.

(10) Patent No.: US 9,047,539 B2
(45) Date of Patent: Jun. 2, 2015

(54) MEDICAL WORKFLOW SYSTEMS AND METHODS WITH PROCESS WORKFLOW RECORDATION

(75) Inventors: Uma S. Ranjan, Bangalore (IN); Alexander Fischer, Aachen (DE); Andrew J. Buckler, Wenham, MA (US); Shuping Xie, Solon, OH (US); Shivakumar Kunigal Ramaswamy, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 1717 days.

(21) Appl. No.: 12/195,669

(22) Filed: Aug. 21, 2008

(65) Prior Publication Data

US 2009/0292559 A1    Nov. 26, 2009

Related U.S. Application Data

(60) Provisional application No. 61/054,858, filed on May 21, 2008.

(51) Int. Cl.
| | |
|---|---|
| *G06Q 10/00* | (2012.01) |
| *G06Q 50/00* | (2012.01) |
| *G06K 9/62* | (2006.01) |
| *G06F 19/00* | (2011.01) |
| *G06Q 50/24* | (2012.01) |

(52) U.S. Cl.
CPC ............ *G06K 9/6284* (2013.01); *G06F 19/321* (2013.01); *G06Q 50/24* (2013.01)

(58) Field of Classification Search
CPC ....................................................... G06K 9/00
USPC ........................................................ 705/2, 3
See application file for complete search history.

(56) References Cited

U.S. PATENT DOCUMENTS

| | | | |
|---|---|---|---|
| 6,574,742 B1* | 6/2003 | Jamroga et al. ............... 713/400 |
| 2002/0071677 A1* | 6/2002 | Sumanaweera ............... 396/429 |
| 2002/0156367 A1* | 10/2002 | Pettersson et al. ............ 600/413 |
| 2004/0162809 A1 | 8/2004 | Koenig |
| 2005/0177394 A1* | 8/2005 | Hosoya et al. .................... 705/2 |
| 2006/0111935 A1 | 5/2006 | Bao et al. |
| 2006/0242144 A1 | 10/2006 | Esham et al. |
| 2006/0293917 A1 | 12/2006 | Bao et al. |
| 2007/0140538 A1* | 6/2007 | Doran et al. .................. 382/128 |
| 2007/0160275 A1 | 7/2007 | Sathyanarayana |
| 2008/0052112 A1 | 2/2008 | Zahlmann et al. |
| 2008/0052126 A1 | 2/2008 | Sasai et al. |

FOREIGN PATENT DOCUMENTS

| | | |
|---|---|---|
| EP | 1903462 A2 | 3/2008 |
| WO | 2007082218 A2 | 7/2007 |

OTHER PUBLICATIONS

Kallman, H-E., et al.; Technical information in digital images; 2008 http://www.europacs.net.

* cited by examiner

*Primary Examiner* — Neha Patel (57) ABSTRACT

A medical information processing and storage system includes a medical images database storing medical images and metadata relevant to the medical images. A processor is configured to perform post-acquisition image processing on medical images. A medical images archiver is configured to store a medical image in the medical images database after the medical image has been processed by the processor. The medical images archiver stores the medical image in the database with processing-descriptive metadata that is descriptive of the post-acquisition image processing performed on the medical image by the processor.

22 Claims, 3 Drawing Sheets

Fig. 3

MEDICAL WORKFLOW SYSTEMS AND METHODS WITH PROCESS WORKFLOW RECORDATION

CROSS REFERENCE TO RELATED APPLICATIONS

This application claims the benefit of U.S. provisional application Ser. No. 61/054,858 filed May 21, 2008, which is incorporated herein by reference.

BACKGROUND OF THE INVENTION

The following relates to the medical arts, information arts, and related arts. It finds application in preclinical studies, in clinical studies, in medical diagnosis and monitoring, and the like.

Medical studies synthesize information from numerous sources. Within a study, various types of information may be generated and synthesized, such as: medical images or other in vivo data; in vitro data such as tests on drawn blood, mass spectrum profiles or the like; ex vivo data such as histology findings; and so forth. Additionally, a medical study may synthesize outside information such as the procedures used in, and results obtained by, similar studies. The information synthesis reviews "comparable" information to detect trends, similarities, or other commonalities possibly indicative of an underlying common pathology or other common condition, and to detect differences or dissimilarities that may contraindicate a common condition or may point to some underlying additional complexity that may impact the findings of the study.

The comparisons should involve "comparable" information. For example, two images may be comparable if they are of the same anatomical region and are acquired using similar geometry and at similar resolution. Any differences between the images, such as different modalities (e.g., comparison of a magnetic resonance image and a computed tomography image), must be considered in making a valid comparison. Since image geometries may not be identical, a registration algorithm may be applied to spatially align corresponding features of images under comparison. Temporal registration may also be performed for comparisons of temporal sequences of images such as cardiac CINE image sequences.

To facilitate making valid comparisons, image information annotations may be stored with the image. Typically, medical images are stored in a database such as a Picture Archive and Communication System (PACS) in a standard format such as the Digital Imaging and Communication in Medicine (DICOM) format promulgated by the National Electrical Manufacturers Association (NEMA, Rosslyn, Va.), or variants of the promulgated format (such variants also sometimes referred to as a DICOM format). The DICOM format includes the image data along with a DICOM header storing information about the image such as modality, resolution, subject identification information, subject demographic information, cataloging information identifying the study or other grouping of which the image is a part, information on any JPEG or other type of image compression or formatting (called "transfer syntax" information in the DICOM standard), modality-specific image acquisition information (such as the echo time, TE, in the case of magnetic resonance images), or so forth.

The DICOM header provides information about the image, which facilitates fair comparison of different images. However, the researcher performing an image comparison must still take care to ensure that the images are comparable respective to other factors, such as post-acquisition image processing operations that may have been performed on the image. Post-acquisition image processing may include, for example, image registration, image segmentation, contrast enhancement, or so forth. Over the course of a given study, the post-acquisition image processing workflow may be altered to improve detection of lesions or other clinically relevant features, or for other reasons. To ensure fair comparisons, such alterations must be taken into account when comparing images modified by different workflows. Comparisons with images from other studies can be even more problematic, since information on the post-acquisition image processing used in other studies may be difficult or impossible to obtain.

In some instances, it would be useful for the researcher to readily locate comparable images from other studies. For example, when a researcher encounters an unusual image that deviates strongly from other images of the study, the researcher will want to understand this deviant image. Understanding might be facilitated by comparison with similar images obtained in other studies. Unfortunately, merely identifying a visually similar image in the PACS database (or elsewhere) is insufficient for a fair comparison. This is true even if the information about the images provided by the DICOM headers is similar. Rather, once a visually similar image is identified in the DICOM database, the researcher must track down the post-acquisition processing workflow (if any) performed on the identified visually similar image in order to determine whether it is fairly comparable with the deviant image of the present study.

The following provides a new and improved apparatuses and methods which overcome the above-referenced problems and others.

SUMMARY OF THE INVENTION

In accordance with one disclosed aspect, a medical information processing and storage system is disclosed, comprising: a medical images database storing medical images and metadata relevant to the medical images; a processor configured to perform post-acquisition image processing on medical images; and a medical images archiver configured to store a medical image in the medical images database after the medical image has been processed by the processor, the medical images archiver storing the medical image with processing-descriptive metadata that is descriptive of the post-acquisition image processing performed on the medical image by the processor.

In accordance with another disclosed aspect, a storage medium is disclosed, storing instructions executable to perform a medical information processing and storage method including performing post-acquisition image processing on a medical image to generate a modified medical image, generating metadata descriptive of the post-acquisition image processing, and storing in a medical images database the modified medical image along with the metadata descriptive of the post-acquisition image processing.

In accordance with another disclosed aspect, a medical information processing and storage system is disclosed, comprising: a medical images database storing medical images and metadata relevant to the medical images; and a medical images archiver configured to store medical images in the medical images database, the medical images archiver configured to store medical images that have undergone post-acquisition image processing together with processing-descriptive metadata that is descriptive of said post-acquisition image processing that has been performed on the medical image.

One advantage resides in providing medical images with traceable post-acquisition image processing.

Another advantage resides in facilitating fair comparison of different medical images.

Another advantage resides in facilitating augmentation of medical images with non-image medical information that has undergone post-acquisition processing similar to the post-acquisition image processing of the medical image.

Still further advantages of the present invention will be appreciated to those of ordinary skill in the art upon reading and understand the following detailed description.

DETAILED DESCRIPTION OF THE INVENTION

Figure 1:
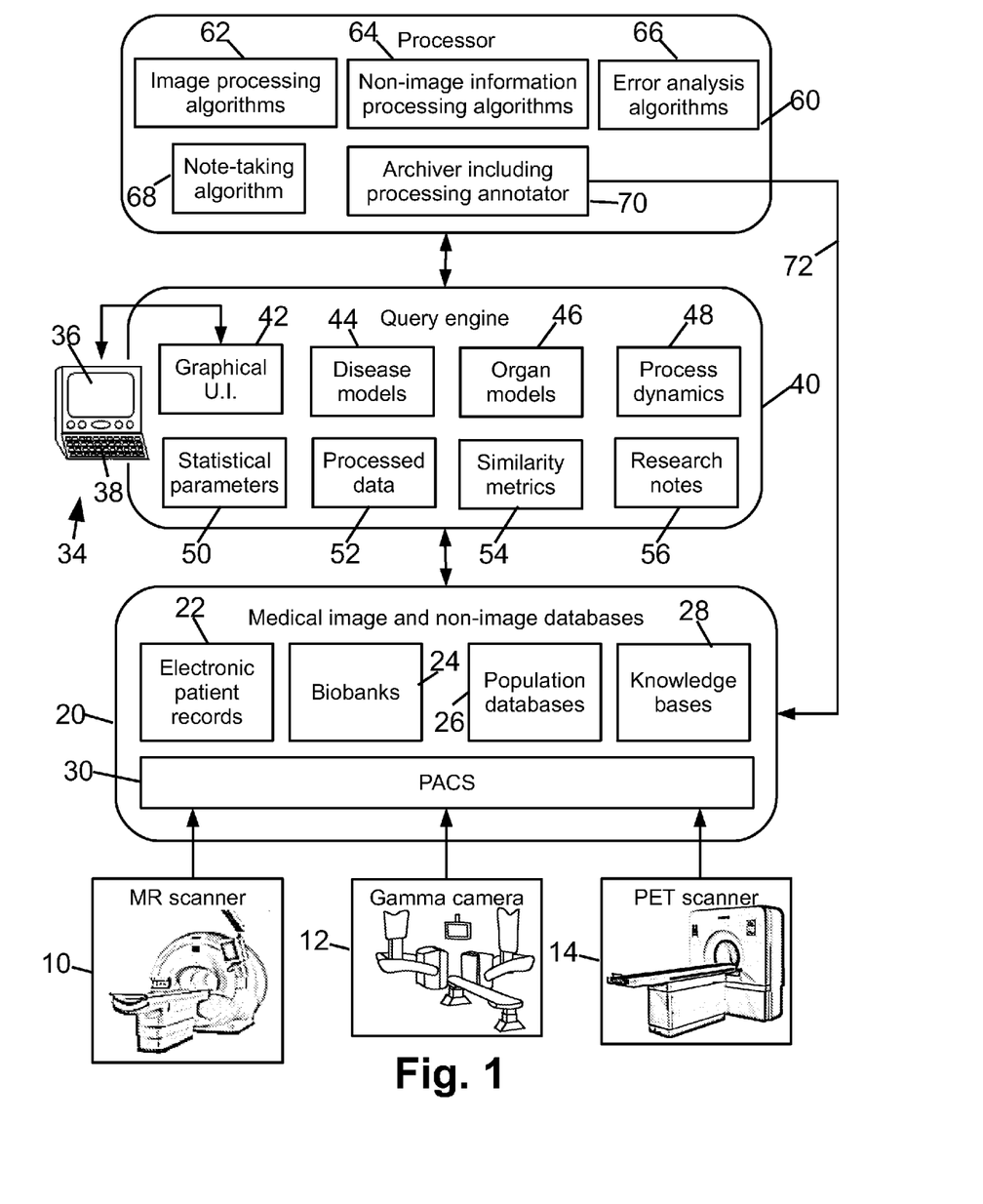
FIG. 1 diagrammatically shows a medical information processing and storage system.

With reference to FIG. 1, a hospital, clinical or pre-clinical research facility, or other medical facility includes one or more medical imaging devices, such as an illustrated magnetic resonance imaging (MRI) scanner 10, a gamma camera 12 for performing nuclear medical imaging techniques such as single photon emission computed tomography (SPECT), and a positron emission tomography (PET) scanner 14. These imagers 10, 12, 14 are illustrative examples, and substantially any imaging modality may be included. Some other known imaging systems, for example, include fluoroscopy imagers, ultrasound imagers, or so forth.

The medical facility further includes or has access to one or more medical image and non-image databases 20, such as the illustrated examples of an electronic patient records (EPR) database 22, one or more biological banks ("Biobanks") 24, one or more population databases 26 providing demographic information, and other knowledge bases 28. Each database may be located either locally on-site or remotely. For example, some of these databases may be located on site, such as the EPR database 22, while other of these databases may be remote and accessed via the Internet or another digital network, such as the Biobanks 24 and demographic databases 26.

A medical images database is provided for storing medical images. In the illustrated embodiment, a Picture Archive and Communication System (PACS) 30 stores images in a standard format such as a Digital Imaging and Communication in Medicine (DICOM) format in accordance with the standard promulgated by the National Electrical Manufacturers Association (NEMA, Rosslyn, Va.), or in accordance with a DICOM format that is a variant of the promulgated standard. In the DICOM format, each image is stored together with a DICOM header providing metadata about the image. The header includes an Information Object Definition (IOD) made up of various Information Entity (IE) metadata attribute sets. For example, an MRI image stored in DICOM format may have a DICOM header with an IOD including an IE defining patient attributes, an IE defining the pre-clinical or clinical study attributes, an IE defining the MRI scanner, an IE defining attributes of the MRI image such as pixels, image plane, magnetic contrast agent bolus identity (if any), and so forth. The headers enable the PACS database 30 to store images generated by different imaging modalities, images of different patients, images related to different studies, and so forth, in the common PACS database 30. Other databases, such as the EPR database 22, for example, can associate images with patients or other groupings by storing pointers or other links to the images stored in the PACS database 30.

To access information stored in the databases 20, a doctor, radiologist, medical researcher, or other user can use a suitable interface device such as an illustrated computer 34 having a display 36 and one or more input devices such as an illustrated keyboard 38, a mouse, trackball, touchpad, a speech recognition unit, or so forth. The interface device 34 includes or interfaces with a query engine 40 to enable querying one or more of the databases 20 using structured query language (SQL) queries or queries conforming with another query syntax or language. The queries are suitably generated via a command line interface, or are constructed using a graphical user interface 42 executing in conjunction with the interface device 34, or by a speech recognition interface, or are generated by a combination of such interfaces. The optional graphical user interface 42 enables a user to construct a query by, for example, selecting parameters from drop-down lists, using graphical selection buttons, check-boxes, or so forth shown on the display 36. The optional graphical user interface 42 optionally enables more complex queries to be entered in a text dialog box or window.

In a typical operation, a doctor, researcher, radiologist, or other user retrieves an image, or a set of images, from the PACS database 30 using a suitable query. For images, such queries can be based on metrics or annotations contained in the DICOM image header, such as patient identity, the identity of the study with which the image is associated, image modality (e.g., MRI, CT, PET, et cetera), or so forth.

As is disclosed herein, the header information is extended versus conventional DICOM headers to include content related to image processing operations. As a result, the query can also relate to such processing operations. For example, an image processed based on a disease model can be queried based on the organ or disease model 44, 46 used in the processing. An image can also be queried based on header annotations descriptive of processing stages or dynamics 48 that the image has been passed through, such as spatial registration operations, post-acquisition contrast enhancement processing, image segmentation operations, or so forth. Other query criteria may include statistical parameters 50 such as the confidence associated with a type of processing. The image data 52 that has been processed through one or more of such methods can itself be the subject of the query criterion, for example by querying to identify image characteristics such as largest connected region, average grayscale level, or so forth. Query criteria can also be comparative, based on similarity metrics 54. For example, a researcher having an image of interest may construct a query to identify images similar to the image of interest with such similarity measured by suitable similarity metrics 54. Queries can also be based on criteria corresponding to research notes or other manual annotations 56 added to an image by previous experimenters. For example, it is contemplated to enable the user to annotate an image with a suspected pathology believed to be present in the image subject.

Although described principally with respect to images, it is further disclosed herein to include header information or other metadata for non-image data so as to include content related to or descriptive of processing operations applied to non-image data such as genome or protein sequences, histology results, or so forth. Accordingly, such non-image data can also be queried both respective to information about the non-image data itself (e.g., molecular sub-sequences, information about the subject identity, or so forth) and respective to information about how the non-image data has been processed (e.g., information about the pH or other parameters used in a protein folding model, information about the chemicals used in histology analyses, or so forth).

An image or set of images acquired by the query engine 40 can be subjected to one or more process operations applied by a processor 60. In the diagrammatic representation of FIG. 1, the processor 60 is shown as a separate element, which may be the case. Alternatively, the processor may be integrated with the interface device 34. As an example of the latter configuration, the interface device 34 may be a computer having a microprocessor or other processing elements (not illustrated in FIG. 1) that run software executable to cooperate with the interfacing devices 36, 38 to perform querying functions of the query engine 40, and the microprocessor or other processing elements further run software executable to perform processing functions of the processor 60. Alternatively, the processor 60 may be a separate component, as shown, for example an Internet-based server including the processor 60 that receives images to be processed from the interfacing device 34 and sends processed images back to the interfacing device 34. Still further, the illustrated processor 60 may be embodied as two, three, or more processors operating cooperatively or independently to perform processing operations. Other embodiments comprise a storage medium, such as an optical disk, magnetic disk, magnetic tape, random access memory (RAM), remote Internet server storage, or the like storing instructions executable by the processor 60 to perform the medical information processing and storage methods disclosed herein.

The processor 60 can perform various image processing algorithms 62, such as for example contrast enhancement, rigid or non-rigid spatial registration, image segmentation, image analysis algorithms such as lesion detection algorithms, or so forth. The processor 60 can also run processing 64 on non-image information such as genome or protein sequences or histology data. The processor 60 can further perform error analysis operations 66, as part of the data processing 62, 64 or in addition thereto. For example, the processor 60 may determine confidence intervals for each processing operation using error analysis algorithms 66 that are integral with the data processing 62, 64, and additionally may determine final confidence intervals for the data after multiple processing operations using suitable error propagation algorithms 66. Optionally, the processor 60 may further execute a text editor, word processor, or other suitable note-taking algorithm 68 to enable a user to input comments on the processed image such as diagnostic or clinical observations relevant to patient diagnosis or a clinical study, respectively, observations regarding the doctor's or researcher's professional opinion as to the identity or possible malignancy of a detected lesion, or so forth. It is to be appreciated that in some instances the processor 60 may perform a sequence of processing operations, and that moreover the doctor, researcher, radiologist, or other user may modify the sequence of processing operations partway through the sequence, or may modify the sequence of processing operations before initiating the sequence, or may modify parameters of one or more of the processing operations of the sequence of processing operations before or partway through the sequence, or may otherwise interact with and modify the processing.

The processor 60 is also configured to define an archiver 70 that adds image header information or other metadata annotations descriptive of the processing operations 62, 64, error analyses 66, and other processing 68 performed by the processor 60. The archiver 70 adds this descriptive information to the DICOM image header or other metadata collection or annotation that is included with the processed image or processed non-image information. The archiver 70 causes the processed image or processed non-image information to be stored 72 in an appropriate database of the set of databases 20, together with the metadata annotations descriptive of those processing operations 62, 64, 66, 68 performed on the processed image or processed non-image information. The storing 72 can entail, for example, writing the processed image together with the processing-descriptive metadata to an optical or magnetic digital data storage medium. In the case of a processed image, the archiver 70 stores the processed image together with a DICOM header including information descriptive of the image processing that the processed image has undergone in the PACS database 30.

In the case of a sequence of process operations, the annotation or set of annotations descriptive of each processing operation are suitably concatenated. In one approach, the output of each image processing operation may be stored in the PACS database 30 together with the concatentation of metadata descriptive of all processing operations performed up to the time that the processed image is stored. If the output of each image processing operation is separately stored, then the PACS 30 will ultimately store a sequence of images corresponding to each step of the sequence of process operations. Alternatively, if the output of each successive image processing operation is stored by overwriting the stored image output by the previous processing operation, then the PACS will store at any given time a single processed image corresponding to the last-completed process operation along with a concatenation of metadata descriptive of all processing that the stored image has undergone. As yet another approach, the intermediate processed images may not be stored at all, but rather the processor 60 may maintain a concatentation of metadata descriptive of all processing operations that have been performed as the sequence of processing operations progresses, and only the final processed image output by the sequence is stored in the PACS database 30 together with the concatenation of metadata descriptive of all processing performed by the completed sequence of processing operations.

Figure 2:
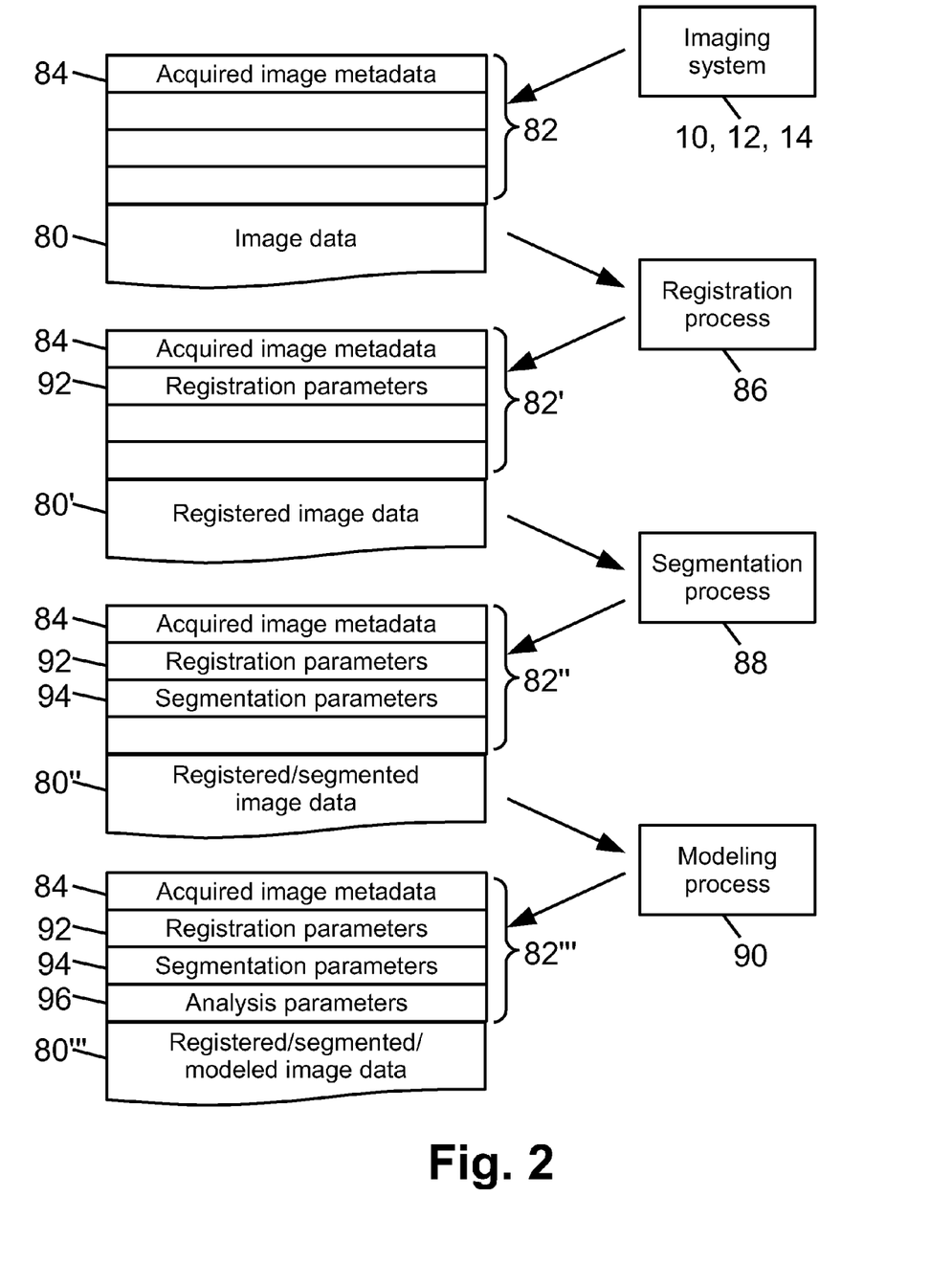
FIG. 2 diagrammatically shows a processing workflow for an image, in which the workflow comprises a sequence of post-acquisition image processing operations.

With reference to FIG. 2, a diagrammatic example of processing an image and appending process-descriptive annotations is set forth. One of the imaging systems 10, 12, 14 acquires a medical image of a subject, as part of a pre-clinical study, part of a clinical study, as a diagnostic for diagnosing a medical patient, as evaluation of ongoing treatment of a pathology of a patient, or so forth. The imaging system stores the image in the PACS 30 in a DICOM format including the image data 80 and a DICOM header 82 including acquired image metadata 84 such as identifying information about the subject, identifying information about the study (in the case in which the image data 80 are acquired as part of a clinical or preclinical study), acquisition parameters used in acquiring the image (such as modality, resolution, et cetera), and so forth. In some embodiments, the acquired image metadata 84 comprises header information organized as various Information Entity (IE) metadata attribute sets arranged in conformance with the DICOM standard or a variant thereof.

A user wishes to model the acquired image using an organ or disease model. Accordingly, the user formulates a query to retrieve the image (optionally along with other images meeting the query criteria) from the PACS database 30, and the image is processed by the processor 60 performing a sequence of processing operations including a spatial registration process 86, an image segmentation process 88, and an image modeling process 90. The spatial registration process 90 is performed first, so as to align the image spatially. This generates first-modified image data 80' comprising the image data 80 modified by the spatial alignment process. In order to ensure that the spatial registration process is documented, registration parameters metadata 92 are added to the image header so as to form a modified DICOM header 82' including a concatenation of the acquired image metadata 84 and the registration parameters metadata 92. These latter parameters 92 may include, for example, designation of any landmarks used in the spatial registration, designation of a reference image or spatial map used in the spatial registration, identification of the particular registration algorithm employed in the spatial registration, identification of whether a rigid or non-rigid registration was performed, and so forth.

In some embodiments, the spatial registration parameters 92 are stored in conformance with a DICOM-compatible Information Entity (IE) metadata attribute set template that defines the ordering and formatting of stored spatial registration parameters and other appropriate format information. This IE metadata template is suitably accessible by both the archiver 70 (so that the archiver 70 can determine how to construct the IE containing the spatial registration parameters 92) and by the query engine 40 (so that the query engine 40 can construct an appropriate query for locating images based on spatial registration parameters should the user request or select such a query). The processed intermediate image 80' together with the metadata 82' comprising the acquired image metadata 84 and the registration parameters metadata 92 is optionally stored in the PACS 30 by overwriting the original image content 80, 82 or by retaining the original image content 80, 82 and adding new image data 80', 82'. In embodiments in which the registration parameters metadata 92 is stored in conformance with a suitable IE template, the processed image data 80', 82' can be stored in a DICOM format, with either no modification to the PACS 30 or with an IE templates database of the PACS 30 modified to include the spatial registration parameters IE template. (Whether such a template should be stored with the PACS 30 depends upon the apportioning of image query and retrieval processing between the query engine 40 and the PACS database 30.)

These processing and archiving operations are repeated for each subsequent step in the sequence of process operations performed by the processor 60. In a next step, the image segmentation process 88 is performed. For example, if the modeling to be performed is respective to a particular anatomical organ, then the image segmentation process 88 suitably delineates or defines the anatomical organ to be modeled. Further processed (that is, registered and segmented) intermediate image data 80" are optionally stored together with a further-modified image header 82" in the PACS database 30, where the further-modified image header 82" includes the aforementioned acquired image metadata 84 and registration parameters metadata 92 and further includes concatenated segmentation parameters metadata 94. If stored, the intermediate image data 80" and associated image header 82" are stored either as a replacement for the previous image data 80', 82' or as a new image. In another embodiment, the concatenated metadata 82" comprising the acquired image metadata 84, the registration parameters metadata 92, and the segmentation parameters metadata 94, are temporarily stored in a buffer or memory of or accessible by the processor 60. The segmentation parameters metadata 94 may include, for example, an identification of the employed segmentation algorithm, any organ model used in the segmentation (for example, an initial "wire-mesh" organ model that is deformed to perform the segmentation in certain types of segmentation algorithms), a grayscale range used in the segmentation (for example, if the segmentation algorithm classifies pixels according to grayscale value as part of the segmentation process), or so forth. In some embodiments, the segmentation parameters metadata 94 are stored in conformance with a segmentation parameters IE template that defines the ordering and formatting of stored parameters and other appropriate format information.

In the final step of the illustrative sequence of process operations, the modeling process 90 is performed. For example, the modeling may entail modeling the anatomy of an organ, or modeling anatomical manifestations of a pathology of interest (for example, modeling any detected tumor or lesion), modeling a cardiac cycle in the case where the image is a cardiac CINE sequence of images, or so forth. The final processed (that is, registered, segmented, and modeled) image data 80''' are stored together with a final image header 82''' in the PACS database 30, where the final image header 82''' includes the acquired image metadata 84, the registration parameters metadata 92, the segmentation parameters metadata 94, and further concatenated analysis parameters metadata 96. The final image data 80''' and associated final image header 82''' are stored either as a replacement for the previous image data 80", 82", or as a replacement for the original unprocessed image 80, 82 (a suitable option if the intermediate images 80', 82", 80", 82" were not stored in the PACS 30), or as a new image. The analysis parameters metadata 96 may include, for example, an identification of the employed modeling algorithm, any organ or disease model used in the modeling, any initial parameters used in an iterative modeling process, or so forth. In some embodiments, the analysis parameters metadata 96 are stored in conformance with an analysis parameters IE template that defines the ordering and formatting of stored parameters and other appropriate format information.

The formatting of the metadata can take various forms. For example, in the embodiment of FIG. 2 the header has a fixed size, and unused portions are left blank. These unused areas can be identified by being filled with zeroes padding or other filler data, or can be identified by including an "end-of-header" delimiter such as a special byte value (e.g., 255) so that a sequential reading of the header will detect the end of the used header space.

Figure 3:
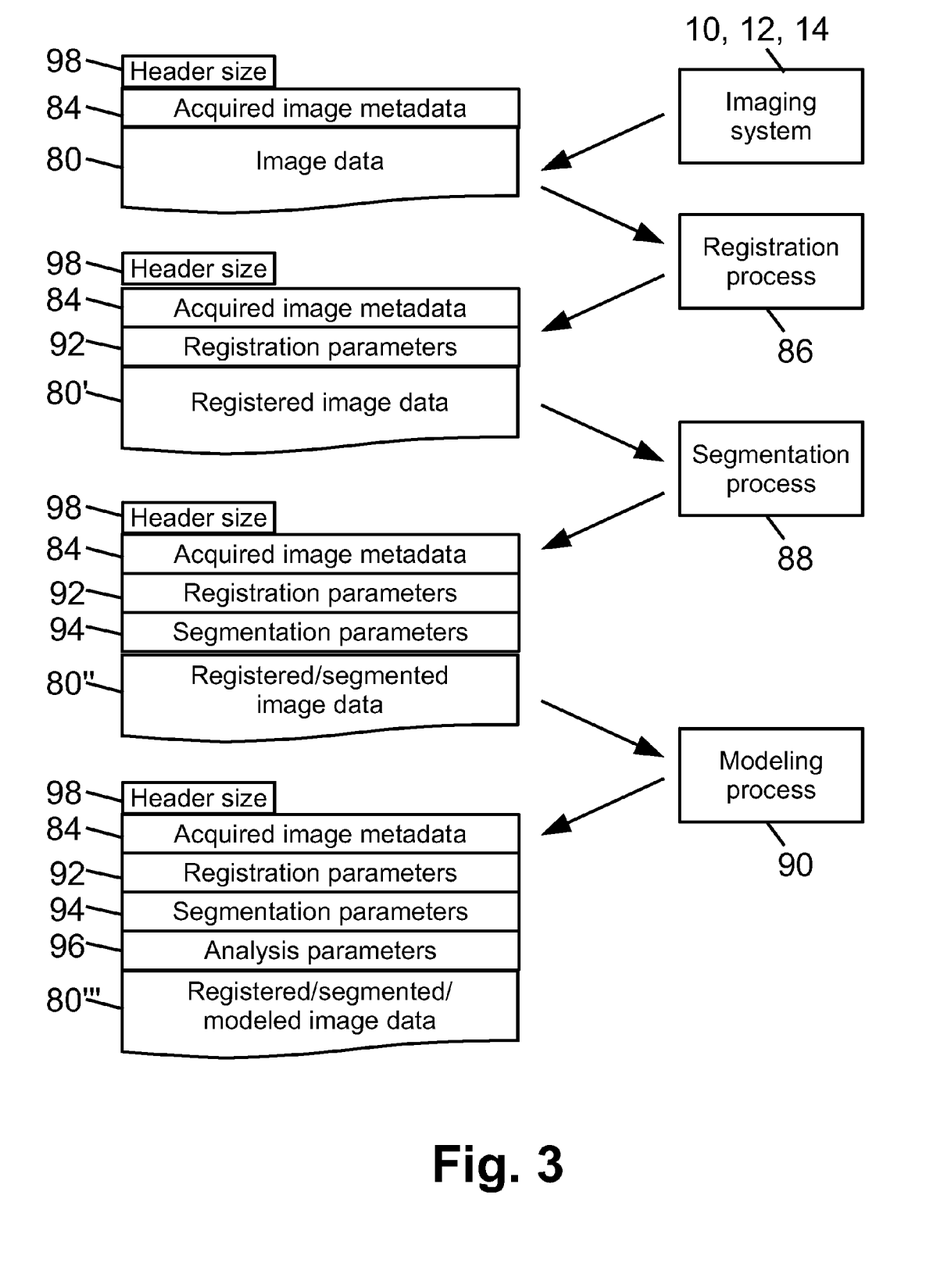
FIG. 3 diagrammatically shows processing workflow of FIG. 2, but using a different format for the metadata stored with the images.

With reference to FIG. 3, in another suitable form, the header has a variable size rather than a fixed size, and a header size parameter 98 contains the length of the header. It is also contemplated to omit the header size parameter 98 and instead rely upon an "end-of-header" delimiter to identify the end of the variable-size header.

These are merely illustrative examples of some suitable formats for storing the information including processing-descriptive information as metadata with the image data. It is also to be appreciated that terms such as "stored together with" and the like encompass both data that is physically stored together and data that is logically linked together by a pointer or the like. For example, it is contemplated to store the metadata headers 82, 82', 82", 82''' of FIG. 2 in one region of a database and to store the image data 80, 80', 80", 80''' in a separate and distinct region of the database, and to provide pointers or logical links to associate together each image 80, 80', 80", 80''' and its corresponding metadata header 82, 82', 82", 82'''. Still further, while the examples of FIGS. 2 and 3 relate to annotation and storage of image data, the disclosed approaches are also optionally employed to annotate and store non-image medical data such as genome or protein sequences, histology results, or so forth with both information about the non-image medical data and post-acquisition processing-descriptive information.

With reference back to FIG. 1, the illustrated system ensures that each image stored in the PACS 30 (and, optionally, each non-image medical information entity stored in a suitable database such as the EPR database 22) is annotated both with information about the image or entity and with information about any post-acquisition processing that the image or entity has undergone between the time of acquisition and the time the image was stored. A doctor, researcher, radiologist, or other user who has an unusual image of interest and wants to locate a similar image for comparison can formulate a suitable query including information about any processing the image of interest has undergone, and the query engine 40 can account for post-acquisition processing of images in the PACS database 30 in making the determination of whether an image from the PACS database 30 is indeed "similar" to the image of interest. This, in turn, ensures that the user does not make invalid comparisons of images that may have coincidental similarity due to convergent results of different processing workflows.

As another application, given the image of interest the user may query the PACS database 30 to identify other images that are similar in respects such as being acquired from similar subjects, being of the same anatomical region, and so forth, but which may have undergone different processing workflows. From this, the user may reprocess the image of interest and/or the identified similar stored images using a common workflow in order to generate images with parallel post-acquisition processing workflows in order to make valid comparisons. Such reprocessing is readily performed if the originally acquired image prior to any post-acquisition processing is stored in the PACS database 30, since the processing-descriptive metadata define the sequence of processing operations making up the workflow. Even if the originally acquired image has been lost (for example, overwritten by an image modified by post-acquisition processing) it may be possible to perform reprocessing if the post-acquisition processing operations are reversible (that is, can be "undone" by performing inverse operations). By reprocessing, images that originally may have appeared dissimilar due to divergent effects of different post-acquisition processing workflows may be identified as being probatively similar.

As another application, the query engine 40 may be configured to retrieve a relevant medical image from the PACS database 30, as already described, and to retrieve relevant medical information other than images from the EPR database 22 or from another medical information database, based on a similarity of the processing-descriptive metadata for the relevant medical image and the processing-descriptive metadata for the relevant medical information other than images. For example, the similarity may include a common disease, pathology, or other model used in both the post-acquisition image processing of the relevant medical image and in the post-acquisition processing of the relevant medical information other than images. In this way, for example, the user having retrieved an image of interest can readily identify non-image medical data that has been processed under the same or similar assumptions (i.e., the same model) that may provide complementary information of value in interpreting or understanding the image of interest.

These are merely illustrative applications. The skilled artisan will find numerous additional advantages and applications for having a database of images or of non-image medical information that is annotated with post-acquisition processing information so as to enable accounting for such post-acquisition processing in data analysis, data comparison, and other usages of such data. For clinical or preclinical studies, at any stage of the workflow it may be useful for a researcher to determine how the current analysis or experiment has performed against other similar experiments in which data is subjected to the same kind of workflow. It is also interesting for a researcher to explore different lines of treatment which have been done following a certain stage of processing of data. Another application is to extract data arising from previous studies, such as organ or disease models, statistical confidence of processing stages or of the entire workflow, data which was processed as a result of a specific type of processing, research notes from previous studies, and so forth. As a result of new studies and experiments, it may also be of interest to update the knowledge base after a suitable validation and standardization.

In the system of FIG. 1, each stage in the workflow generating a particular image (or non-image medical information entity) is characterized by annotations using qualitative descriptive information such as model type, algorithm type or so forth, and quantitative descriptive information such as model parameters, calibration factors and so forth, which model the transformation of the image by post-acquisition processing workflow. This metadata is stored as annotations to the processed image or entity with such processing-descriptive information maintained for each stage in the workflow. For images, this metadata may be stored as part of the DICOM header. For non-image medical data other metadata annotation formats may be used. By concatenating data from each processing step, the processing-descriptive information is maintained for each stage in the workflow. For a sequence of processing steps, that is, a work flow, the annotations can include metadata specifying a confidence interval or probability for the entire sequence by taking into account and annotating error propagation. Optionally, the annotations may also include text data or other informal or non-standardized content such as research notes. This information also can be queried by the query engine 40. A complete or partial workflow is suitably annotated by concatenating the process-descriptive metadata of each stage in the order of the stages until the final stage (in the case of a complete workflow) or until the last-completed stage (in the case of a partial workflow).

In this way, a query to a database such as PACS 30 can obtain images that have undergone a similar workflow, or to identify a prospective workflow for specific experiments, or to update a workflow as a part of experiment design. Such an update may be performed before or partway through an experiment, so as to adjust or modify the workflow portion that has not yet been executed. For processing steps, the modifications may include the type of processing (that is, the processing steps can be added, deleted, or replaced), or the parameters associated with a processing step yet to be performed. For error probabilities and statistical confidence, such updates may include updating error probabilities (or the method of computing such error probabilities) associated with each processing stage. For workflow design, modifications may include the possibility to specify the impact of a particular stage on the overall workflow.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A medical information processing and storage system comprising:
a medical images database storing digital medical images and metadata relevant to the digital medical images;
a processor configured to perform post-acquisition image processing on digital medical images; and
a medical images archiver configured to store a digital medical image in the medical images database after the digital medical image has been processed by the processor, the medical images archiver storing the digital medical image with processing-descriptive metadata that is descriptive of the post-acquisition image processing performed on the digital medical image by the processor.

2. The system as set forth in claim 1, further comprising:
a query engine configured to retrieve digital medical images from the medical images database based on a query at least in part on metadata descriptive of selected post-acquisition image processing.

3. The system as set forth in claim 2, further comprising:
a graphical user interface at least assisting the user in selecting the query.

4. The system as set forth in claim 2, wherein the query engine is configured to retrieve digital medical images from the medical images database based on a similarity metric based at least in part on similarity of metadata descriptive of post-acquisition image processing.

5. The system as set forth in claim 2, further comprising:
a display configured to display the digital medical images retrieved from the medical images database by the query engine.

6. The system as set forth in claim 1, wherein the medical images database stores digital medical images and metadata relevant to the digital medical images in a Digital Imaging and Communication in Medicine (DICOM) format, and the medical images archiver is configured to store the digital medical image with a DICOM header including the processing-descriptive metadata.

7. The system as set forth in claim 6, wherein the medical images archiver is configured to store in the DICOM header the processing-descriptive metadata by concatenating attributes descriptive of post-acquisition image processing operations in an order of performance of the post-acquisition image processing operations.

8. The system as set forth in claim 1, wherein the medical images archiver is configured to store a first digital medical image with first processing-descriptive metadata that is descriptive of post-acquisition image processing performed on the first digital medical image by the processor, and is further configured to store a second digital medical image comprising the first digital medical image further processed by additional post-acquisition image processing, the second digital medical image being stored with the first processing-descriptive metadata and concatenated additional processing-descriptive metadata that is descriptive of the additional post-acquisition image processing.

9. The system as set forth in claim 8, wherein medical images archiver replaces the first digital medical image with the second digital medical image in the medical images database.

10. The system as set forth in claim 1, further comprising:
a medical information database storing medical information other than digital medical images and metadata relevant to the medical information other than digital medical images, the processor further configured to perform post-acquisition processing on at least some medical information other than digital medical images; and
a medical information archiver configured to store medical information other than digital medical images in the medical information database after the medical information has been processed by the processor, the medical information archiver storing the medical information other than digital medical images with non-image processing-descriptive metadata that is descriptive of post-acquisition processing performed on the medical information by the processor.

11. The system as set forth in claim 10, wherein the system further comprises:
a query engine configured to retrieve a relevant digital medical image from the medical images database and relevant medical information other than digital medical images from the medical information database based on a similarity of the processing-descriptive metadata for the relevant digital medical image and the processing-descriptive metadata for the relevant medical information other than digital medical images.

12. A non-transitory storage medium storing instructions executable to perform a medical information processing and storage method including performing post-acquisition image processing on a digital medical image to generate a modified digital medical image, generating metadata descriptive of the post-acquisition image processing performed on the digital medical image, and storing in a medical images database the modified digital medical image along with the metadata descriptive of the post-acquisition image processing performed on the digital medical image.

13. The non-transitory storage medium as set forth in claim 12, wherein:
the performing includes performing a plurality of post-acquisition image processing operations on the digital medical image to generate the modified digital medical image; and
the generating comprises generating one or more metadata attributes descriptive of each post-acquisition image processing operation and concatenating the metadata attributes to define the metadata descriptive of the post-acquisition image processing performed on the digital medical image.

14. The non-transitory storage medium as set forth in claim 12, wherein the performed method further comprises:
after the storing, performing additional post-acquisition image processing on the modified digital medical image to generate a further modified digital medical image;
generating additional metadata descriptive of the additional post-acquisition image processing performed on the modified digital medical image; and
storing in the medical images database the further modified digital medical image along with the metadata descriptive of the post-acquisition image processing performed on the digital medical image and along with the additional metadata descriptive of the additional post-acquisition image processing performed on the modified digital medical image.

15. The non-transitory storage medium as set forth in claim 14, wherein the storing of the further modified digital medical image replaces the modified digital medical image in the medical images database.

16. The non-transitory storage medium as set forth in claim 12, wherein the performed method further comprises:
constructing a DICOM header including a first set of attributes defining image-descriptive metadata and a second set of attributes defining the metadata descriptive of the post-acquisition image processing performed on the digital medical image, the storing operation storing the modified digital medical image in the medical images database in a DICOM format including the constructed DICOM header.

17. The non-transitory storage medium as set forth in claim 16, wherein the post-acquisition image processing performed on the digital medical image comprises a plurality of post-acquisition image processing operations performed on the digital medical image, and the second set of attributes comprises a concatenation of the metadata descriptive of each post-acquisition image processing operation performed on the digital medical image.

18. The non-transitory storage medium as set forth in claim 12, wherein the performed method further comprises:
  retrieving a digital medical image from the medical images database based on a retrieval criterion based at least in part on metadata descriptive of selected post-acquisition image processing performed on the digital medical image; and
  displaying the retrieved digital medical image.

19. The non-transitory storage medium as set forth in claim 12, wherein the performed method further comprises:
  performing post-acquisition non-image processing on non-image medical information to generate modified non-image medical information;
  generating metadata descriptive of the post-acquisition non-image processing; and
  storing in a non-image medical information database the modified non-image medical information along with the metadata descriptive of the post-acquisition non-image processing.

20. A medical information processing and storage system comprising:
  a medical images database storing medical images and metadata relevant to the medical images; and
  a medical images archiver configured to store medical images in the medical images database, the medical images archiver configured to store medical images that have undergone post-acquisition image processing together with processing-descriptive metadata that is descriptive of said post-acquisition image processing that has been performed on the medical image;
  wherein the medical images archiver is configured to store processing-descriptive metadata corresponding to each of a plurality of post-acquisition processing operations ordered in a temporal order of performance of the post-acquisition processing operations.

21. The system as set forth in claim 20, further comprising:
  a query engine configured to retrieve medical images from the medical images database based on a query at least in part on metadata descriptive of selected post-acquisition image processing.

22. The system as set forth in claim 20, wherein the medical images database stores medical images and metadata relevant to the medical images in a DICOM format, and the medical images archiver is configured to store the medical image with a DICOM header including the processing-descriptive metadata.

\* \* \* \* \*